(12) United States Patent
Chong Rodriguez et al.

(10) Patent No.: US 10,456,080 B2
(45) Date of Patent: Oct. 29, 2019

(54) PADDED, FLEXIBLE ENCASING FOR BODY MONITORING SYSTEMS IN FABRICS

(71) Applicant: Bloomer Health Tech., Inc., Dover, DE (US)

(72) Inventors: Alicia Chong Rodriguez, Cambridge, MA (US); Monica Lucia Abarca Abarca, Lima (PE)

(73) Assignee: Bloomer Health Tech., Inc., Dover, DE (US)

( * ) Notice: Subject to any disclaimer, the term of this patent is extended or adjusted under 35 U.S.C. 154(b) by 0 days.

(21) Appl. No.: 15/642,583

(22) Filed: Jul. 6, 2017

(65) Prior Publication Data

US 2018/0317845 A1    Nov. 8, 2018

Related U.S. Application Data

(60) Provisional application No. 62/501,826, filed on May 5, 2017.

(51) Int. Cl.
*A61B 5/00* (2006.01)
*A61B 5/024* (2006.01)
*A61B 5/0402* (2006.01)
*A61B 5/08* (2006.01)

(52) U.S. Cl.
CPC ........ *A61B 5/6801* (2013.01); *A61B 5/02438* (2013.01); *A61B 5/683* (2013.01); *A61B 5/6804* (2013.01); *A61B 5/002* (2013.01); *A61B 5/024* (2013.01); *A61B 5/0402* (2013.01); *A61B 5/08* (2013.01)

(58) Field of Classification Search
CPC ... A61B 5/6801; A61B 5/683; A61B 5/02438; A61B 5/6804; A61B 5/002; A61B 5/024; A61B 5/08; A61B 5/0402; H01R 4/64; H01R 4/58; Y10S 439/909; Y10S 2/905
USPC .............................. 439/651, 37, 909; 2/905
See application file for complete search history.

(56) References Cited

U.S. PATENT DOCUMENTS

| | | | | |
|---|---|---|---|---|
| 3,960,138 A | * | 6/1976 | Doss ........................ | A61B 5/01 600/549 |
| 5,386,616 A | * | 2/1995 | Norvell .................. | A44B 19/32 24/384 |
| 6,019,877 A | * | 2/2000 | Dupelle ............... | A61N 1/0492 204/196.11 |
| 6,419,636 B1 | * | 7/2002 | Young .................... | A61B 5/015 600/372 |

(Continued)

*Primary Examiner* — Tulsidas C Patel
*Assistant Examiner* — Travis S Chambers
(74) *Attorney, Agent, or Firm* — Bachman & LaPointe, P.C.

(57) ABSTRACT

A wearable monitoring device comprising a printed circuit board having a first side and a second side opposite the first side, wherein the printed circuit board is configured to couple to at least one sensor configured to monitor a physiological condition; a first padding layer coupled to the printed circuit board proximate the first side; a second padding layer coupled to the printed circuit board proximate the second side; a first protective layer coupled to the first padding layer opposite the printed circuit board; a second protective layer coupled to the second padding layer opposite the printed circuit board, the first protective layer and the second protective layer seal together and enclose the first and second padding and the printed circuit board; a power source coupled to the printed circuit board.

16 Claims, 4 Drawing Sheets

(56) References Cited

U.S. PATENT DOCUMENTS

| | | | |
|---|---|---|---|
| 7,878,030 B2* | 2/2011 | Burr | D04B 1/14 66/173 |
| 8,945,328 B2* | 2/2015 | Longinotti-Buitoni | A61B 5/0002 156/234 |
| 2007/0208542 A1* | 9/2007 | Vock | A43B 3/0005 702/187 |
| 2011/0197331 A1* | 8/2011 | Reynolds | A41B 17/00 2/69 |
| 2013/0085347 A1* | 4/2013 | Manicka | A61B 5/0205 600/301 |
| 2016/0353810 A1* | 12/2016 | Barnes | A41C 3/0057 |

* cited by examiner

PADDED, FLEXIBLE ENCASING FOR BODY MONITORING SYSTEMS IN FABRICS

CROSS-REFERENCE TO RELATED APPLICATION

This application claims the benefit of U.S. Provisional Application Ser. No. 62/501,826, filed May 5, 2017.

BACKGROUND

The present disclosure is directed to a wearable monitoring device that is integrated into clothing and configured to detect and communicate measurements of a person's electrophysiology.

Cardiovascular diseases cause more deaths globally than cancer, HIV and malaria combined. Infections, metabolic, respiratory and cardiac diseases, cancers and other illnesses are all massive problems that can be better tackled with continuous and event monitoring and personalized information of the patient for an efficient diagnosis.

Prior solutions include devices that can monitor certain body functions worn on the body. Those solutions attempt to address the issues of comfort and durability. Those past solutions include electronics that are bulky, stiff and uncomfortable. Typically, the batteries and microelectronics are stored in a hard case that is unyielding and difficult to integrate into clothing. Those systems are especially not easily integrated into clothing that is worn frequently, such as undergarments.

What is needed are clothes integrated with a comfortable device to obtain the status of the human body for prevention of cardiovascular diseases by tracking real time information of the heart to help deal with diseases and optimize health by making clothes intelligent and useful.

SUMMARY

In accordance with the present disclosure, there is provided a wearable monitoring device comprising a printed circuit board having a first side and a second side opposite the first side, wherein said printed circuit board is configured to couple to at least one sensor configured to monitor a physiological condition; a first padding layer coupled to said printed circuit board proximate the first side; a second padding layer coupled to said printed circuit board proximate the second side; a first protective layer coupled to said first padding layer opposite said printed circuit board; a second protective layer coupled to said second padding layer opposite said printed circuit board, said first protective layer and said second protective layer seal together and enclose said first and second padding and said printed circuit board; and a power source coupled to said printed circuit board.

In another and alternative embodiment, a garment having a wearable monitoring device comprising the wearable monitoring device coupled to said garment, wherein said wearable monitoring device comprises a printed circuit board having a first side and a second side opposite the first side, wherein said flexible printed circuit board comprises a microprocessor configured to process electrophysiological measurements and biometric measurements and wirelessly transmit said electrophysiological measurements and biometric measurements to another device selected from the group consisting of a computer, a mobile phone, a recording device and the like; a first padding layer coupled to said flexible printed circuit board proximate the first side; a second padding layer coupled to said printed circuit board proximate the second side; a first protective layer coupled to said first padding layer opposite said printed circuit board; a second protective layer coupled to said second padding layer opposite said printed circuit board, said first protective layer and said second protective layer sealing together and enclosing said first and second padding and said flexible printed circuit board; and at least one sensor coupled to said wearable monitoring device and said garment, said at least one sensor configured to monitor a physiological condition through inputs of said electrophysiological measurements and biometric measurements.

In another and alternative embodiment, a process for monitoring a physiological condition comprising donning a garment having a wearable monitoring device over a portion of a wearer's body, said wearable monitoring device comprising a printed circuit board having a first side and a second side opposite the first side; a first padding layer coupled to said printed circuit board proximate the first side; a second padding layer coupled to said printed circuit board proximate the second side; a first protective layer coupled to said first padding layer opposite said printed circuit board; a second protective layer coupled to said second padding layer opposite said printed circuit board, said first protective layer and said second protective layer sealing together and enclosing said first and second padding and said printed circuit board; a power source coupled to said printed circuit board; monitoring at least one physiological condition of said wearer with at least one sensor coupled to said wearable monitoring device and said garment; sending a signal including data of said physiological condition; and processing said signal and transmitting said signal to a collection device.

Other details of the wearable monitoring device are set forth in the following detailed description and the accompanying drawing wherein like reference numerals depict like elements.

DETAILED DESCRIPTION

Figure 1:
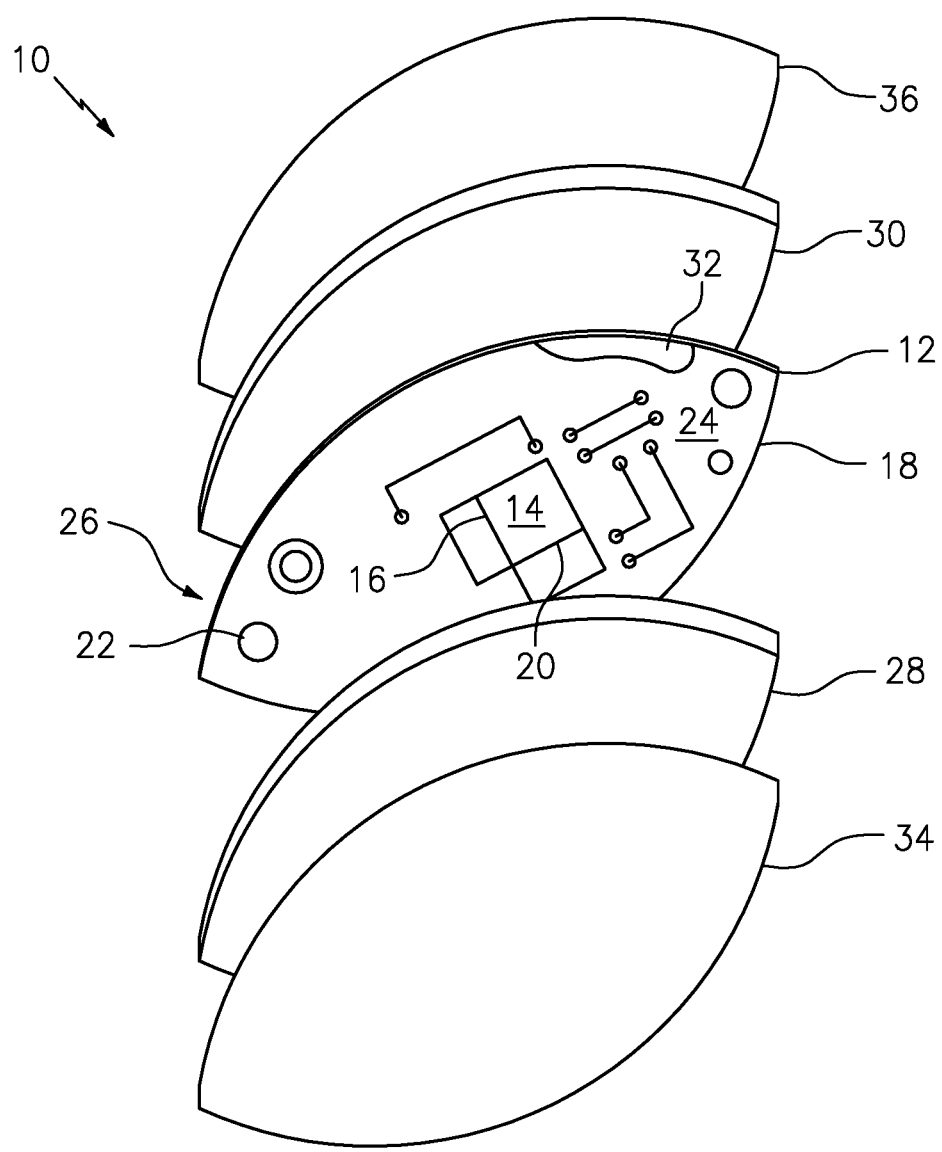
FIG. 1 is an exploded view of an exemplary wearable monitoring device.

Referring now to FIG. 1, there is illustrated an exploded view of an exemplary wearable monitoring device 10. The wearable monitoring device 10 comprises a printed circuit board 12. The printed circuit board 12 can include a processing unit 14 having at least one microprocessor 16 built into a substrate 18. A printed circuit board (PCB) mechanically supports and electrically connects electronic components using conductive tracks, pads and other features etched from copper sheets laminated onto a non-conductive substrate. Components (e.g. capacitors, resistors or active devices) are generally soldered on the PCB. Advanced PCBs may contain components embedded in the substrate. The PCB can include, laminates, copper-clad laminates, resin impregnated B-stage cloth (Pre-preg), and copper foil. The printed circuit board 12 can be made of a flexible material or from a less flexible material or a rigid material. The printed circuit board 12 can include materials such as any kind Rigid PCB with a substrate such as a Flame Retardant, CEM, PTFE; a flex PCB (pyralux, Kapton, copper-clad foil or can be laminated to a thin stiffener) and the combination of both which can be a Rigid Flex. The processing unit 14 can comprise one or more processors 16, a memory 20, and input/output of electric or electronic signals 22. The printed circuit board 12 can include a first side 24 and a second side 26 opposite the first side 24

The printed circuit board 12 can be sandwiched between a first padding layer 28 coupled to said printed circuit board 12 proximate the first side 24. A second padding layer 30 can be coupled to the printed circuit board 12 proximate the second side 26. The first and second padding layers 28, 30 can be selected from the group consisting of foam, silicon, a material having a cellular structure resistant to electrostatic discharge (ESD) material (i.e., polyurethane), and memory foam, gelatinous material and poly laminate foam that protects the circuit board 12 from water and is comfortable and safe next to a body.

In an alternative embodiment, the printed circuit board 12 can include a thin film cover 32 that envelopes and protects the circuit board 12 from electrostatic discharge and water.

A first protective layer 34 can be coupled, bonded, laminated or layered to the first padding layer 28 opposite the printed circuit board 12. A second protective layer 36 can be coupled, bonded (i.e., tricot bonded), laminated or layered to the second padding layer 30 opposite the flexible printed circuit board 12. The first protective layer 34 and the second protective layer 36 are sealed together and enclose the first and second padding layers 28, 30 and the printed circuit board 12. The first protective layer 34 and the second protective layer 36 can be fabrics (i.e., waterproof polyurethane laminated (PUL) fabrics), soft advanced fabrics, hydrophobic material, and the like.

Figure 2:
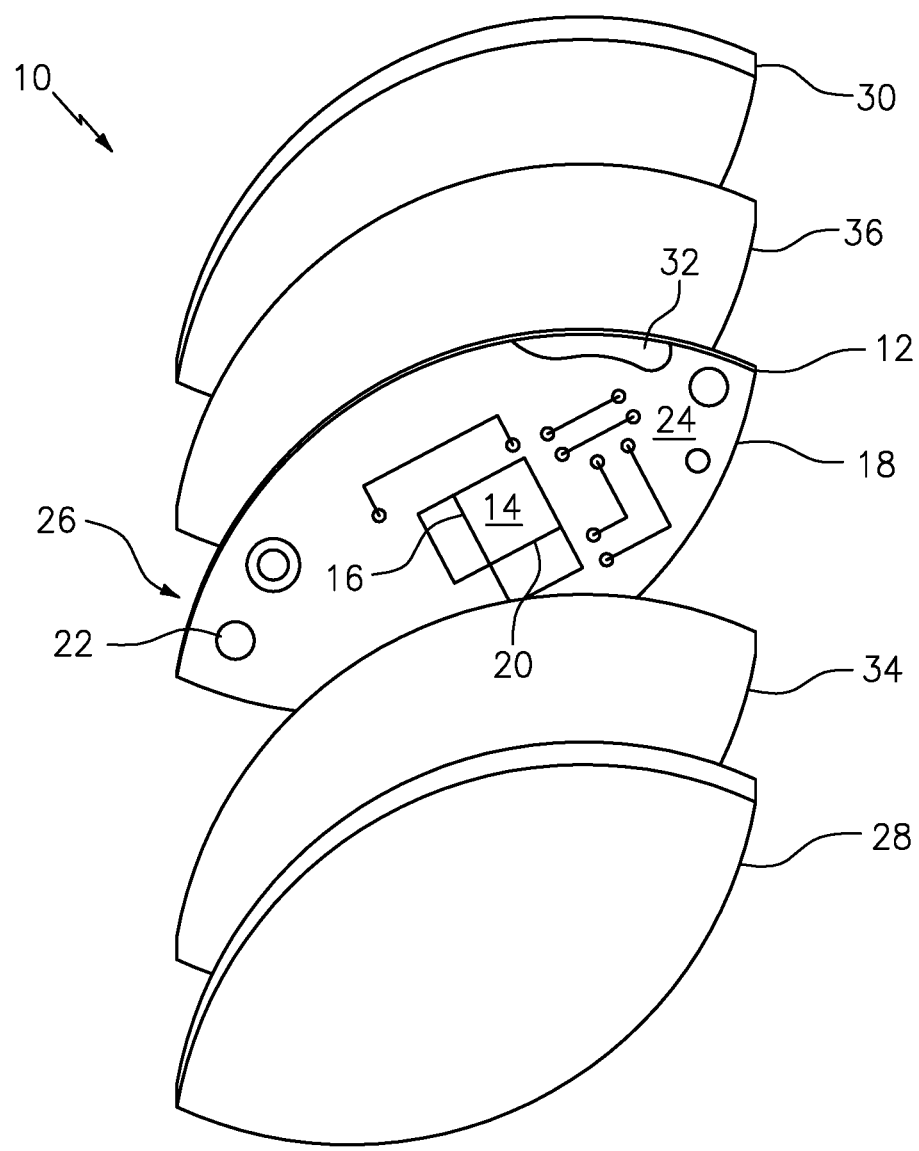
FIG. 2 is an exploded view of an exemplary wearable monitoring device.

In an alternative embodiment as shown in FIG. 2 the first protective layer 34 and second protective layer 36 can be placed closest to the printed circuit board 12. The first and second padding layers 28, 30 can be placed on against the first and second protective layers 34, 36 opposite the printed circuit board 12 respectively. The first and second protective layers 34, 36, can be coupled to the printed circuit board 12 to seal and protect the printed circuit board 12 from moisture and contaminants.

Figure 3:
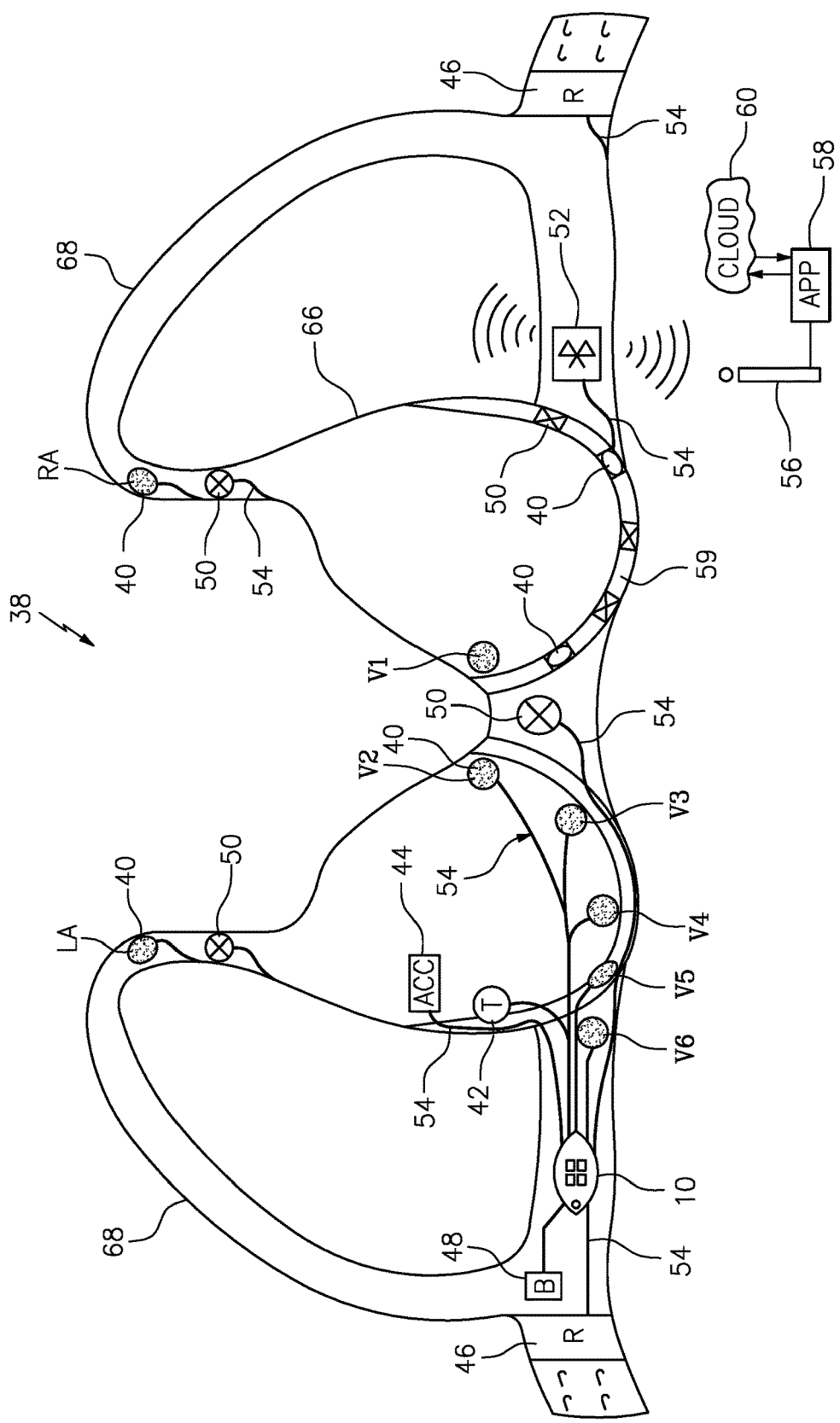
FIG. 3 is an illustration of a garment integrated with an exemplary wearable monitoring device and various sensors and transceiver.

The combination of the protective layers 34, 36 and padding layers 28, 30 surrounding the flexible printed circuit board 12 make up a uniquely wearable monitoring device 10 that can be easily integrated into a garment 38 as shown in FIG. 3.

The garment 38 is shown as an exemplary embodiment, as a bra and can also be any form of garment 38 that is used proximate the body, preferably the torso. Such examples of garments 38 include a brassiere, bustier, bra, corset, babydoll, bralette, basque, bodice torsolette, sports bra, panties, boxers, shirts, pants, jeans, jackets, sweaters, hats, socks and the like.

The garment 38 can include a variety of sensors 40 designed to sense a person's electrophysiology, biological features and the like. The sensors 40 can include at least one or more of the following: textile or fiber integrated sensors, acoustic sensors, position sensors, optical sensors, piezo resistive sensors, temperature sensors, electrocardiogram electrodes, accelerometer, piezo resistive fabric, microphones and the like. The sensors 40 can be configured to obtain status of the human body for prevention of diseases by tracking real time information of the heart, hereunder at least one or more of the following: heart rate, heart rate variability, heart rate recovery, electrocardiogram (in the following referred to as ECG), heart sound; lungs, hereunder at least one or more of the following: respiratory rate, minute ventilation, maximal oxygen consumption, lungs sounds; body metrics, at least one or more of temperature, movements, position, and the like.

The exemplary embodiment shown at FIG. 3 includes a variety of sensors 40, specifically a temperature sensor 42, an accelerometer 44, a piezo resistive sensor 46, electrophysiological sensors, V1, V2, V3, V4, V5, V6, LA, RA and the like.

A power source 48, such as a battery is shown coupled to the wearable monitoring device 10. The wearable monitoring device 10 can be coupled to the various sensors 40 and power source 48, switches 50, and wireless communicator or transceiver 52 by use of a conductor 54, such as conductive thread, wire and the like.

In addition to the sensors 40, the transceiver 52 can include, Wi-Fi™, BLUETOOTH® wireless communication and/or other RF equipment wirelessly coupled to another transceiver 56, user interface, such as a smartphone 58, and cloud 60 and has the possibility of connecting to servers, computers, supercomputers or others for AI (artificial intelligence), machine learning and other data processing/interpreting methods. The data collected by the various sensors 40 can be processed by the microprocessor which can perform some low embedded machine learning algorithms 16 and transmitted by the transceiver 52 to transceiver 56 and shared through an application on the smartphone 58, displayed by using algorithms to provide valuable content.

The processing unit 16, the memory 20, the user interface 58, the one or more biometric sensors 40, and the input/output interface 22 may be communicatively connected via communications path(s). It is to be understood that some of these components may also be connected with one another indirectly. In some embodiments, components of FIG. 1 may be implemented as an external component communicatively linked to other internal components. For instance, in one embodiment, the memory 20 may be implemented as a memory on a secondary device such as a computer or smartphone that communicates with the device wirelessly or through wired connection via the I/O interface 22. In another embodiment. The user interface 58 may include some components on the device such as a switch 50, as well as components on a secondary device communicatively linked to the device via the I/O interface 22, such as a touch screen on a smart phone 58, or smart watch and the like. The raw data from the sensors 40 can pass through a processing stage that can include filters, operational and instrumental amplifiers and instrumental, analog to digital converters, analog front end and the like.

In another exemplary embodiment, the sensors 40 can be integrated with a bra wire casing 59. The bra wire casing 59 can include a textile material formed into a tube for receiving a bra wire (not shown) that is utilized to stiffen and support the garment 38. The sensors 40 and casing 59 can be integrated into a unit an integrated with the other sensors 40 of the garment 38.

Figure 5:
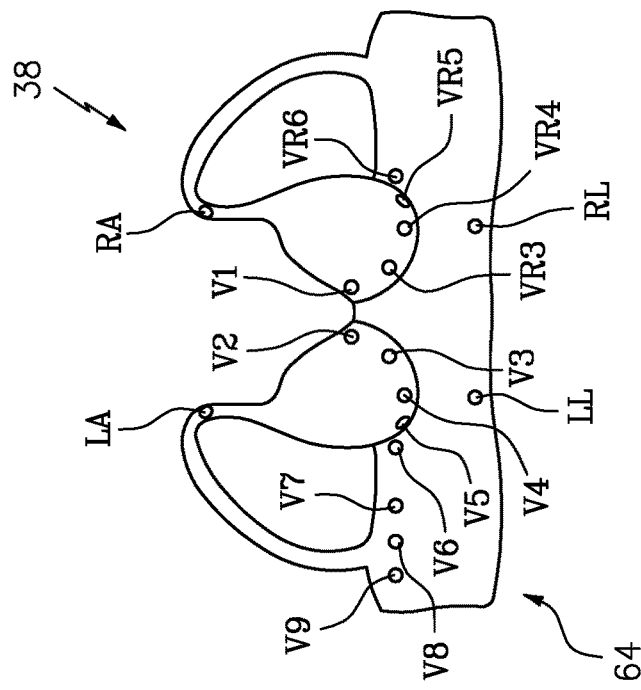
FIG. 5 is an illustration of an exemplary garment.
Figure 4:
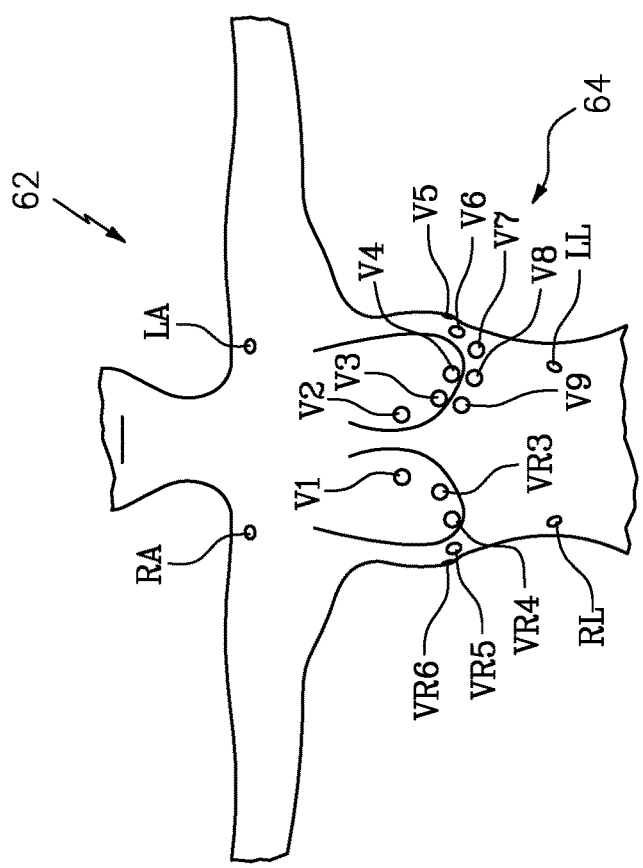
FIG. 4 is an illustration of an exemplary wearer.

FIG. 4 and FIG. 5 illustrate a wearer 62 and the garment 38 and the variety of sensors 40 placed in locations 64 understood to be optimal for electrophysiological measurement of the cardiovascular system of the body. The American Heart Association (AHA) and International Electrotechnical Commission include electrode positions for electrocardiogram or other cardiovascular measurements. The garment 38 can include sensor 40 locations following these guidelines.

The electrode positions (AHA lead wire labels/IEC labels, and the drawings are shown with AHA labels).

Electrode positions are commonly known as follows:

RA/R: Middle to outside end of the right clavicle, close to the bone;

LA/L: Middle to outside end of the left clavicle, close to the bone;

RL/N: Lower right trunk, just above the hip;

LL/N: Lower left trunk, just above the hip;

V1/C1: $4^{th}$ intercostal space at right border of the sternum;

V2/C2: $4^{th}$ intercostal space at left border of the sternum;

V3/C3: midway between V2 and V4;

V4/C4: $5^{th}$ intercostal space at midclavicular line;

V5/C5: level with V4 at left anterior axillary line;

V6/C6: level with V4-V5 at left midaxillary line;

VR3/C3R: midway between V1 and V4R;

VR4/C4R: $5^{th}$ intercostal space, right midclavicular line;

VR5/C5R: level with V4R at right anterior axillary line;

VR6: level with VR4-VR5 at right midaxillary line

V7/C7: level with V4R at right anterior axillary line;

V8/C8: level with V4-V6 at left midscapular line;

V9/C9: level with V4-V6 at left spinal border.

Different electrode positions can be used to make measurements of the electrocardiogram different leads such as follows:

Bipolar limb leads (frontal plane):

Lead 1: RA (−) to LA(+) (Right Left, or lateral).

Lead II: RA (−) to LL(+) (Superior Inferior).

Lead Ill: LA(−) to LL(+) (Superior Inferior).

Augmented unipolar limb leads (frontal plane):

Lead aVR: RA (+) to [LA & LL] (−)(Rightward).

Lead aVL: LA(+) to [RA & LL] (−)(Leftward).

Lead aVF: LL (+) to [RA & LA] (−) (Inferior).

Unipolar(+) chest leads (horizontal plane):

Leads V1, V2, V3: (Posterior Anterior).

Leads V4, VS, V6: (Right Left, or lateral.

The wearable monitoring device 10 can be inserted in the brassier in a cup 66, the device 10 can be removable (from a pocket of thin textile) and/or sewn or embedded in the cup 66 itself, options will be available, the first and second protective layer 34, 36 can be replaced by a similar feeling textile with the device 10 inside, connected to two electrodes 40 in diverse positions. In another exemplary embodiment, the wearable monitoring device 10 can comprise the entire cup 66 as a single unit. The entire cup 66 with device 10 can be removable, integrated or a stand-alone unit.

There are many configurations of single-lead electrodes near the chest area, that covers all the positions of the recent ecg patches can be placed at (such as delta epatch, mc10, and other patches for arrythmias) the wearable monitoring device can have positions as above and can be inserted in the brassiere as part of the garment 38.

This monitoring device can be used for the inner-lining of padded bras and as cup input, replacement or complement, its padding component can come in many ranges of thickness, if padding is thick enough the flexible printed circuit board can be changed for a regular printed circuit board, as long as it is still not noticeable to the user and comfortable. A Single-lead configuration can include any two electrodes in different electrode positions (i.e., LA and RA).

In an alternative embodiment, the flexible circuit board 12 can be located under the arm, on the side of the bra 38 (left or right), or in the cup 66 or in the back. The flexible circuit board 12 is removable from a pocket and/or sewn. Several multiple lead configurations are available, including some or all of the lead-placements (also could be referred to as the combination of two or more diverse single-lead positions mentioned above).

In an alternative embodiment, the switches 50 can be configured as mechanical push button, touch sensor, and the like (round or square or other shape) and placed in 1, 2 and/or 3 strategic places:

a. 1 switch 50: in the mid-center of the bra 38 or on the left or right side of a bra strap 68 and the cup 66.

b. 2 switches 50: mid-center of the bra 38 and either the left or right side of the bra strap 68 and the cup 66 or left and right sides of the bra strap 68 and the cup 66.

c. 3 switches 50: mid-center of the bra 38 and left and right sides of the bra strap 68 and the cup 66.

In an alternative embodiment, the multiple switches 50 can be utilized as follows:

When in a 24-hour ECG Monitoring process (continuous monitoring): when the switch 50 is pushed by the wearer the device 10 stores the set of data in special format (flags/tags) the next flow of data from the heart and other sensors 40 for a time frame of at least 30 seconds to maximum 10 minutes depending on wearer's preferences, therefore if they feel a symptom or need to share a specific moment the data is tagged by use of the switch 50 and saved as priority automatically after pushing the switch 50 without opening an application or the need of any additional devices beyond the bra 38 itself.

Resting ECG: The wearer 62 lies down or gets into a resting position (i.e., seated) and pushes the switch 50 while a recording is made for a time frame of at least 30 seconds to maximum 2 minutes, depending on wearer's profile preferences.

Stress ECG: The user exercises either on a treadmill machine or bicycle and pushes the switch 50 and records for a time frame of at least 30 seconds to maximum 30 minutes depending on user preferences.

Event ECG: During non-continuous monitoring, the wearer 62 presses a direct record switch 50 and the device 10 records and stores the heart's electrical activity taking events at different moments at any part of the wearer's day for a time frame of at least 30 seconds to maximum 2 minutes depending on preferences and quantity of pushes during an event.

Event Recorder+Direct communication: During non-continuous monitoring, the wearer 62 presses a direct record switch and the device 10 records and stores the heart's electrical activity. The information can be sent to the physician or caregiver over the cloud 60 immediately.

The wearable monitoring device 10 can be utilized to obtain status of the human body for prevention and monitoring of cardiovascular diseases by tracking real time information of the heart, hereunder at least one or more of the following: heart rate, heart rate variability, heart rate recovery, electrocardiogram (in the following referred to as ECG), heart sound; lungs, hereunder at least one or more of the following: respiratory rate, minute ventilation, maximal oxygen consumption, lungs sounds; body metrics, hereunder at least one or more of the following: temperature, movements, position.

The wearable monitoring device 10 is configured to improve the measurements of the human body done through sensors, hereunder at least one or more of the following: textile or fabrics integrated sensors, acoustic sensors, position sensors, optical sensors, piezo resistive sensor, temperature sensor. The sensors are connected to protected circuits hereunder at least one or more of the following: protected circuit boards, flexible, semi rigid or rigid printed circuit boards. The sensors and the protected circuits will be placed seamlessly within clothes.

The advantages of the wearable monitoring device is to configure a bra with sensors and washable circuits, because it is located in the critical anatomical sections of the body allowing for monitoring of the heart, lungs and more. The bra will monitor critical health parameters of women, empowering them by providing information critical to their bodies. Since bras are worn daily, the wearable monitoring device will deliver valuable and meaningful, out of the care provider's office continuous and/or event based information of cardiac health, respiratory health and more, in a seamless and safe way.

Another advantage of the wearable monitoring device is that it comprises washable flexible padded encasing for circuits to be used in daily clothing, being an unnoticeable additional material attached to the daily clothing and keeping the comfort and utility of the daily clothing, by being seamless and not interfering with how the clothing is normally used.

The wearable monitoring device may be inserted into, removed from and sewn into a plurality of compatible garments (e.g., brallettes, brassieres, camisole tops). It can be easily integrated as padding, as the cup or a clothing component, sewn or removable, in garments. The device integrates into textiles, fabrics and clothing, it is soft flexible insertable and sewn, leaving behind the use of hard, bulky devices that are attached separately to garments.

This advanced device can be a cup of a bra, which is the fabric covering the breast of women. It can be integrated in a smooth way that is not noticeable to the user in a variety of bra types and coverage levels such as full coverage, a percentage of coverage (medium coverage), demi or balconette or others such as almond shape, eye, and or triangular shaped cups and even a flat squared or round shape.

This monitoring device can be used for the inner-lining of padded bras and as cup input, replacement or complement, its padding component can come in many ranges of thickness, if padding is thick enough the flexible printed circuit board can be changed for a regular printed circuit board, as long as it is still not noticeable to the user and comfortable.

There has been provided a wearable monitoring device. While the wearable monitoring device has been described in the context of specific embodiments thereof, other unforeseen alternatives, modifications, and variations may become apparent to those skilled in the art having read the foregoing description. Accordingly, it is intended to embrace those alternatives, modifications, and variations which fall within the broad scope of the appended claims.

What is claimed is:

1. A wearable monitoring device comprising:
a printed circuit board having a first side and a second side opposite the first side, wherein said printed circuit board is configured to couple to at least one sensor configured to monitor a physiological condition;
a first padding layer coupled to said printed circuit board proximate the first side, said first padding layer being selected from a group consisting of foam, silicon, gelatinous material and poly laminate foam;
a second padding layer coupled to said printed circuit board proximate the second side, said second padding layer being selected from a group consisting of foam, silicon, gelatinous material and poly laminate foam;
a first protective layer coupled to said first padding layer opposite said printed circuit board;
a second protective layer coupled to said second padding layer opposite said printed circuit board, said first protective layer and said second protective layer seal together and enclose said first padding layer and second padding layer and said printed circuit board; and
a power source coupled to said printed circuit board.

2. The device according to claim 1, wherein said printed circuit board comprises at least one microprocessor built into at least one of a flexible substrate, a semi-rigid substrate and a rigid substrate.

3. The device according to claim 1, wherein said first and second protective layer are selected from a group consisting of hydrophobic material, waterproof polyurethane laminated fabric, and the like.

4. The device according to claim 1, wherein said at least one sensor is configured to take electrophysiological measurements and biometric measurements.

5. The device according to claim 4, wherein said electrophysiological measurements and biometric measurements are selected from a group consisting of electrocardiogram, heart rate, heart rate variability, heart rate recovery, respiratory rate, temperature, body position, respiration, activity, movement, and the like.

6. The device according to claim 5, wherein said printed circuit board comprises a microprocessor configured to process said electrophysiological measurements and biometric measurements and wirelessly transmit said electrophysiological measurements and biometric measurements to another device selected from a group consisting of a computer, a mobile phone, a recording device and the like.

7. A garment comprising a bra having a wearable monitoring device comprising:
the wearable monitoring device coupled to said bra, such that the wearable monitoring device is proximate a V6 or VR6 location of a body, wherein said wearable monitoring device comprises a flexible printed circuit board having a first side and a second side opposite the first side, wherein said flexible printed circuit board comprises a microprocessor configured to process electrophysiological measurements and biometric measurements and wirelessly transmit said electrophysiological measurements and biometric measurements to another device selected from a group consisting of a computer, a mobile phone, a smart watch, a recording device and the like; a first protective layer coupled to said flexible printed circuit board proximate the first side; a second protective layer coupled to said flexible printed circuit board proximate the second side; a first padding layer coupled to said first protective layer opposite said flexible printed circuit board; a second padding layer coupled to said second protective layer opposite said flexible printed circuit board, wherein said first protective layer and said second protective layer are selected from a group consisting of foam, silicon, gelatinous material and poly laminate foam; said first protective layer and said second protective layer sealing together and enclosing said flexible printed circuit board; and
at least one sensor coupled to said wearable monitoring device and said garment, said at least one sensor located on said bra such that locations of said at least one sensor correspond to locations for electrophysiological measurement of the body, said at least one sensor configured to monitor a physiological condition through inputs of said electrophysiological measurements and biometric measurements.

8. The garment according to claim 7, further comprising a transceiver configured to receive and transmit said electrophysiological measurements and biometric measurements to said another device that comprises wireless technology for exchanging data, RF signal and the like.

9. The garment according to claim 7, wherein the garment is configured to fit over a torso of a wearer, and configured to align said at least one sensor on said body at locations selected from a group consisting of electrophysiological sensors, V1, V2, V3, V4, V5, V6, V7, V8, V9, LA, RA, LL, RL, VR3, VR4, VR5 and VR6.

10. The garment according to claim 9, wherein said first and second protective layer are selected from a group consisting of hydrophobic material, waterproof polyurethane laminated fabric, and the like.

11. A process for monitoring a physiological condition comprising:
- donning a garment configured as a bra having a wearable monitoring device over a portion of a wearer's body, said wearable monitoring device being located on a side of the bra or in the cup of the bra, said wearable monitoring device comprising a printed circuit board having a first side and a second side opposite the first side;
- a first protective layer coupled to said printed circuit board proximate the first side;
- a second protective layer coupled to said printed circuit board proximate the second side;
- a first padding layer coupled to said first protective layer opposite said printed circuit board, said first padding layer being selected from a group consisting of foam, silicon, gelatinous material and poly laminate foam;
- a second padding layer coupled to said second protective layer opposite said printed circuit board, said second padding layer being selected from a group consisting of foam, silicon, gelatinous material and poly laminate foam, said first protective layer and said second protective layer sealing together and enclosing said printed circuit board; said first padding layer and said second padding layer enclosing said first protective layer and said second protective layer; and
- a power source coupled to said printed circuit board;
- monitoring at least one physiological condition of said wearer with at least one sensor coupled to said wearable monitoring device and said garment;
- sending a signal including data of said physiological condition; and
- processing said signal and transmitting said signal to a collection device.

12. The process of claim 11, further comprising:
- attaching said wearable monitoring device to said garment; and
- detaching said wearable monitoring device from said garment.

13. The process of claim 11, wherein said wearable monitoring device is configured as washable and non-rigid.

14. The process of claim 11, wherein said monitoring comprises obtaining a status of a human body for prevention, monitoring and treatment of cardiovascular diseases including tracking real time information of a heart, comprising at least one of a heart rate, a heart rate variability, a heart rate recovery, an electrocardiogram, a heart sound; and a lung function including at least one of a respiratory rate, a minute ventilation, a maximal oxygen consumption, a lung sound; a body metric, including at least one of a temperature, a body movement, and a body position.

15. The process of claim 11, further comprising:
- utilizing at least one switch to change said monitoring at least one physiological condition of said wearer with at least one sensor coupled to said wearable monitoring device and said garment.

16. The process of claim 15, wherein said at least one switch is utilized to configure said wearable monitoring device to monitor selected from a group consisting of continuous monitoring, Resting ECG monitoring, Stress ECG monitoring, Event Recorder+Direct communication monitoring and the like.

* * * * *